(12) United States Patent
Hogendoorn et al.

(10) Patent No.: US 10,466,086 B2
(45) Date of Patent: Nov. 5, 2019

(54) METHOD FOR OPERATING A NUCLEAR-MAGNETIC FLOWMETER AND NUCLEAR MAGNETIC FLOWMETER

(71) Applicant: Krohne AG, Basel (CH)

(72) Inventors: Cornelis Johannes Hogendoorn, Spijk (NL); Rutger Reinout Tromp, Dordrecht (NL); Lucas Matias Ceferino Cerioni, Dordrecht (NL); Marco Leendert Zoeteweij, Hendrik-Ido-Ambach (NL); Olaf Jean Paul Bousché, Dordrecht (NL)

(73) Assignee: KROHNE AG, Basel (CH)

( * ) Notice: Subject to any disclaimer, the term of this patent is extended or adjusted under 35 U.S.C. 154(b) by 85 days.

(21) Appl. No.: 15/609,138

(22) Filed: May 31, 2017

(65) Prior Publication Data
US 2017/0343403 A1 Nov. 30, 2017

(30) Foreign Application Priority Data

May 31, 2016 (DE) .......................... 10 2016 109 993

(51) Int. Cl.
| | | |
|---|---|---|
| *G01F 1/716* | (2006.01) | |
| *G01N 24/08* | (2006.01) | |
| *G01R 33/563* | (2006.01) | |
| *G01F 15/02* | (2006.01) | |

(52) U.S. Cl.
CPC .............. *G01F 1/716* (2013.01); *G01F 15/02* (2013.01); *G01N 24/08* (2013.01); *G01R 33/56308* (2013.01)

(58) Field of Classification Search
CPC ......... G01N 24/08; G01F 15/02; G01F 1/712; G01R 33/56308; G01R 33/563; G01R 33/302; G01R 33/307
See application file for complete search history.

(56) References Cited

U.S. PATENT DOCUMENTS

| | | | | |
|---|---|---|---|---|
| 4,621,234 A | * | 11/1986 | Caprihan | G01R 33/563 324/306 |
| 4,782,295 A | | 11/1988 | Lew | |
| 6,452,390 B1 | * | 9/2002 | Wollin | G01F 1/716 324/306 |

(Continued)

*Primary Examiner* — Patrick Assouad
*Assistant Examiner* — Demetrius R Pretlow
(74) *Attorney, Agent, or Firm* — David S. Safran; Roberts Mlotkowski Safran Cole & Calderon, P.C.

(57) ABSTRACT

A method for operating a nuclear-magnetic flowmeter in which, when determining a velocity of the medium through a measuring tube, the dependency on properties or the state of a medium is at least reduced. The method exciting a first volume of the magnetized medium flowing at a first velocity within a first measuring section to nuclear-magnetic resonances and a first signal sequence is formed characterizing the nuclear-magnetic resonances of the medium in the first volume, and then, exciting a second volume of the magnetized medium flowing at a second velocity within the first measuring section is excited to nuclear-magnetic resonances and a second signal sequence is formed characterizing the nuclear-magnetic resonances of the medium in the second volume. A quotient sequence is determined from each of the first and second signal sequences, and the first velocity and/or the second velocity is/are determined using the quotient sequence.

16 Claims, 6 Drawing Sheets

(56) References Cited

U.S. PATENT DOCUMENTS

| | | |
|---|---|---|
| 2004/0140800 A1 | 7/2004 | Madio et al. |
| 2006/0213283 A1 | 9/2006 | Morris et al. |
| 2007/0164737 A1* | 7/2007 | Pusiol .................... G01R 33/44 324/306 |
| 2011/0001474 A1 | 1/2011 | Miller et al. |
| 2012/0092006 A1* | 4/2012 | Li ........................ G01N 24/081 324/306 |
| 2014/0015526 A1 | 1/2014 | Bouscké et al. |
| 2016/0202100 A1 | 7/2016 | Hogendoorn et al. |

* cited by examiner

METHOD FOR OPERATING A NUCLEAR-MAGNETIC FLOWMETER AND NUCLEAR MAGNETIC FLOWMETER

BACKGROUND OF THE INVENTION

Field of the Invention

The invention relates to a method for operating a nuclear-magnetic flowmeter. The nuclear-magnetic flowmeter thereby has a measuring tube with at least one first measuring section for carrying out the method. In the method, a medium is made to flow through the measuring tube and the medium in the measuring tube is magnetized.

Description of Related Art

The invention also relates to nuclear-magnetic flowmeters. The nuclear-magnetic flowmeters have a measuring tube, a magnetization means and a measuring means, wherein the measuring tube has at least one first measuring section. During operation of the nuclear-magnetic flowmeter, a medium flows through the measuring tube and the magnetization means magnetizes the medium in the measuring tube.

A nuclear-magnetic flowmeter uses nuclear-magnetic resonance methods for analyzing and, in particular, for measuring the flow of a medium through the measuring tube. Nuclear-magnetic resonance methods influence the precession of atomic nuclei of a medium in the presence of a macroscopic magnetic field, which has been previously magnetized, by exciting the atomic nuclei by means of an electromagnetic pulse affecting the medium and evaluating the effect of the excitation on the atomic nuclei. A nuclear-magnetic flowmeter thus has a magnetization means for generating a magnetic field in a medium flowing through the measuring tube and has a measuring means for exciting the medium in the measuring tube and for measuring the effect of the excitation on the medium in the measuring tube. The measuring means is thereby also designed to carry out the method for operating a nuclear-magnetic flowmeter.

The atomic nuclei of the elements having a nuclear spin also have a magnetic moment caused by the nuclear spin. Nuclear spin can be regarded as an angular momentum describable by a vector, and accordingly, the magnetic moment can also be described by a vector that is aligned parallel to the vector of the angular momentum. The vector of the magnetic moment of the atomic nucleus precesses around the vector of the macroscopic magnetic field, such as the one generated by the magnetization means, at the location of the atomic nucleus. The frequency of precession is called the Larmor frequency $\omega_L$ and is proportional to the value of the magnetic field strength B. The Larmor frequency is calculated according to $\omega_L = \gamma \cdot B$, wherein $\gamma$ is the gyromagnetic ratio, which is at a maximum for hydrogen atom nuclei.

Nuclear-magnetic flowmeters measure the flow of a medium through the measuring tube. The flow of the medium relates either to a volume flow or to a mass flow, wherein both the volume flow and the mass flow are determined, in each case, using a density of the medium and a velocity of the medium in the measuring tube. Methods known from the prior art for operating a nuclear-magnetic flowmeter and known nuclear-magnetic flowmeters determine a velocity of a medium in a measuring tube in that a volume of the magnetized medium within a measuring section are excited to nuclear magnetic resonances and a signal sequence is formed. The signal sequence is thereby formed in that signals are determined that characterize the nuclear-magnetic resonances of the medium in volumes within the measuring section. The signals in the signal sequence subside over time, wherein the subsiding of the signals is influenced, in particular, by two factors. The first factor describes the subsiding of the signals over time essentially based on interaction of the nuclear spin of the atomic nuclei of the medium. This factor is dependent on the properties and the state of the medium, wherein the state, in particular, is described by the temperature of the medium. The second factor describes the subsiding of the signals over time based on the excited medium flowing out of the measuring section. This factor thus includes information about the velocity of the medium, whereas the first factor compromises this information.

SUMMARY OF THE INVENTION

An object of the present invention is thus to provide methods for operating a nuclear-magnetic flowmeter as well as to provide nuclear-magnetic flowmeters, in which, when determining a velocity of a medium through the measuring tube, the dependency on properties and/or the state of a medium is at least reduced.

The invention relates, firstly, to methods for operating nuclear-magnetic flowmeters, in which the derived and described object is achieved. Such nuclear-magnetic flowmeters have a measuring tube with at least a first measuring section.

A first method according to a teaching of the invention for operating a nuclear-magnetic flowmeter with a measuring tube, wherein the measuring tube has a first measuring section, is initially and essentially characterized by the following method steps, which are carried out when a medium is made to flow through the measuring tube and the medium in the measuring tube is magnetized:

In a first method step, a first volume of the magnetized medium flowing at a first velocity within the first measuring section is excited to nuclear-magnetic resonances and a first signal sequence is formed in that at least one signal characterizing the nuclear-magnetic resonances of the medium in the first volume within the first measuring section is determined.

In a second method step, temporally following the previous method step, a second volume of the magnetized medium flowing at a second velocity within the first measuring section is excited to nuclear-magnetic resonances and a second signal sequence is formed in that at least one signal characterizing the nuclear-magnetic resonances of the medium in the second volume within the first measuring section is determined.

In a third method step, a quotient sequence is determined in that a quotient is determined from each the at least one signal of the first signal sequence and the at least one signal of the second signal sequence.

In a fourth method step, either the first velocity and the second velocity are determined using the quotient sequence or the first velocity or the second velocity is determined using the quotient sequence. The method determines the first velocity and/or the second velocity, if, during execution of the method, the first velocity of the medium during the first method step and the second velocity of the medium during the second method step are different.

A second method according to a teaching of the invention, an alternative to the above teaching for operating a nuclear-magnetic flowmeter with a measuring tube, wherein the measuring tube has a first measuring section and a second measuring section, is initially and essentially characterized by the following method steps, which are carried out when a medium is made to flow through the measuring tube and the medium in the measuring tube is magnetized:

In a first method step, a first volume of the magnetized medium within the first measuring section is excited to nuclear-magnetic resonances and a first signal sequence is formed in that at least one signal characterizing the nuclear-magnetic resonances of the medium in the first volume within the first measuring section is determined.

In a second method step, which can be carried out both after the above-described method step as well as simultaneously or overlapping with the method step, a second volume of the magnetized medium within the second measuring section is excited to nuclear-magnetic resonances and a second signal sequence is formed in that at least one signal characterizing the nuclear-magnetic resonances of the medium in the second volume within the second measuring section is determined.

In a third method step, a quotient sequence is determined in that a quotient is determined from each of the at least one signal of the first signal sequence and the at least one signal of the of the second signal sequence.

In a fourth method step, a velocity of the medium is determined using the quotient sequence.

The teaching according to the first method and the teaching according to the second method have essential similarities. According to both methods, a first volume and a second volume of the magnetized medium within measuring sections are excited to nuclear-magnetic resonances and a first signal sequence and a second signal sequence are formed in that, in each case, at least one signal characterizing the nuclear-magnetic resonances of the medium in the respective volume within the respective measuring section is determined. Also, according to both methods, a quotient sequence is determined, in that, in each case, a quotient is determined from the at least one signal of the first signal sequence and from the at least one signal of the second signal sequence and velocities of the flowing medium are determined using the quotient sequence.

The two methods differ in that, according to the first method, only one measuring section is used, which is why the first signal sequence and the second signal sequence have to be determined successively and in that, according to the second method, at least two measuring sections, namely the first measuring section and the second measuring section are used, which is why the first signal sequence and the second signal sequence can be determined either successively or simultaneously or overlapping.

An advantage of the method according to the invention as opposed to the method known from the prior art is that the determined velocities have a lower dependency on properties and on the state of the medium. This relates, in particular, to the temperature of the medium. The lower dependency of determined velocities on properties and on the state of the medium results from the described determination of the quotient sequence. If, for example, both the first signal sequence and the second signal sequence consist of a first signal and a second signal, the quotient sequence is determined in that a first quotient is determined from the first signal of each the first signal sequence and the second signal sequence and a second quotient is determined from the second signal of each the first signal sequence and the second signal sequence. If both the first signal sequence and the second signal sequence have more than two signals, the quotient sequence is accordingly determined.

The first measuring section and the second measuring section according to the second method have, for example, same or different lengths, wherein the first measuring section and the second measuring section do not overlap. If the first and the second measuring section have the same length, then a velocity of the medium during the first method step and a velocity of the medium during the second method step have to be different. If the lengths differ, this is not necessary, however, is also not inhibiting. Preferably, the first measuring section and the second measuring section are spaced from one another by a distance. If the second measuring section is located after the first measuring section in the direction of flow of the medium in the measuring tube, then the distance is preferably greater than the length of the second measuring section. In this manner, it is ensured that the second volume of the magnetized and excited medium has already flowed out of the second measuring section before the first volume of the magnetized and excited medium flows into the second measuring section. If the first volume and the second volume of the magnetized and excited medium are simultaneously located in the second measuring section, the second signal sequence is compromised by a contribution of the first volume of the magnetized and excited medium within the second measuring section.

The first signal sequence and the second signal sequence are each formed in that at least one signal characterizing the nuclear-magnetic resonances of the medium in the respective volume within the respective measuring section is determined. In a first implementation of the method according to the invention, either it is provided that, in each case, a free induction decay is measured as the at least one signal in the first signal sequence and as the at least one signal in the second signal sequence or it is provided that a free induction decay is measured as the at least one signal in the first signal sequence or as the at least one signal in the second signal sequence. Free induction decay is abbreviated to FID. A free induction decay is a nuclear-magnetic resonance and is excited by an electromagnetic pulse, which is suitable for turning vectors of the magnetic moments of the atomic nuclei of the magnetized medium, for example, to 90° in respect to the vector of the magnetic field.

In a further development of the previous implementation, either it is provided that, in each case, an echo signal is measured as at least one further signal in the first signal sequence and as at least one further signal in the second signal sequence, or it is provided that an echo signal is measured as at least one further signal in the first signal sequence or as at least one further signal in the second signal sequence. An echo signal is a further nuclear-magnetic resonance and is excited by an electromagnetic pulse that is suitable for turning vectors of the magnetic moments of the atomic nuclei of the magnetized medium, for example, to 180° in respect to the vector of the magnetic field.

Thus, a signal sequence is composed of at least one signal. If a signal sequence composed of at least a first signal and second signal temporally following the first signal, then it is appropriate that a free induction decay is measured as first signal and an echo signal is measured as second signal. If the signal sequence has further signals after, in terms of time, the second signal, then it is appropriate to measure the further signals as echo signals. As an alternative, a free induction decay is measured, in each case, as the first signal as well as the second signal and/or the further signals.

In order to measure the signals in the signal sequences, measurements of nuclear-magnetic resonances are carried out on the excited medium within each of the measuring sections. In a further implementation of the method, either it is provided that, for determining the at least one signal in the first signal sequence and the at least one signal in the second signal sequence, a measurement is carried out on the medium over an interval and the measurement is integrated over the interval or an average is formed over the measurement or it is provided that, for determining the at least one signal in the first signal sequence or the at least one signal in the second signal sequence, a measurement is carried out on the medium over an interval or the measurement is integrated over the interval or an average is formed over the measurement.

In principle, it is sufficient when each of the signal sequences, in each case, has only one, sole signal. Then, however, it is appropriate that the method is not carried out only once, but repeatedly. In a further implementation, on the other hand, either it is provided that the first signal sequence and the second signal sequence are formed in that at least two signals are determined in each case. If both the first signal sequence and the second signal sequence each have at least two signals, then the quotient sequence has at least two quotients and it is then appropriate that the quotient sequence is interpolated by a function. The function is then, for example, determined from a product of several base functions. For example, polynomial functions and exponential functions are used as base functions. If the quotient sequence consists of at least two quotients, then it is also appropriate that the quotient sequence is approximated using a Taylor polynomial.

To further improve the accuracy of determination of a velocity of the medium flowing through the measuring tube, it is provided in a further implementation that a temperature of the medium is determined and the temperature is used in determining the quotient sequence.

Furthermore, the method according to the invention creates the possibility for determining a spin-spin relaxation time constant of the medium. The spin-spin relaxation time constant is, in particular, dependent on the temperature of the medium and influences the first factor that describes the subsiding of the signals. For this reason, it is provided in a further implementation of the method according to the invention that the spin-spin relaxation time constant of the medium is determined using the quotient sequence and/or using the at least one signal of the first signal sequence and/or using the at least one signal of the second signal sequence.

The invention relates to nuclear-magnetic flowmeters, in which the derived and describe object is achieved. The nuclear-magnetic flowmeters have a measuring tube, a magnetizing means and a measuring means. Thereby, the measuring tube has at least a first measuring section. During operation of a nuclear-magnetic flowmeter, a medium flows through the measuring tube and the magnetization means magnetizes the medium in the measuring tube.

Such a nuclear-magnetic flowmeter, in which the measuring tube has a first measuring section, is initially and essentially characterized, according to a further teaching of the invention, in that the measuring means is designed, during operation, to excite a first volume flowing at a first velocity of the magnetized medium within the first measuring section to nuclear-magnetic resonances and to form a first signal sequence, in that the measuring means determines at least one signal characterizing the nuclear-magnetic resonances of the medium in the first volume within the first measuring section. The measuring means is further designed, then, to excite a second volume flowing at a second velocity of the magnetized medium within the first measuring section to nuclear-magnetic resonances and to form a second signal sequence, in that the measuring means determines at least one signal characterizing the nuclear-magnetic resonances of the medium in the second volume within the first measuring section. Furthermore, the measuring means is designed first to determine a quotient sequence, in that the measuring means determines a quotient from each of the at least one signal of the first signal sequence and the at least one signal of the of the second signal sequence, and, second, to determine the first velocity and/or second velocity using the quotient sequence.

A nuclear-magnetic flowmeter in which the measuring tube has a first measuring section and a second measuring section is initially and essentially characterized, according to a teaching of the invention alternative to the previous teaching, in that the measuring means is designed, during operation, to excite a first volume of the magnetized medium within the first measuring section to nuclear-magnetic resonances and to form a first signal sequence, in that the measuring means determines at least one signal characterizing the nuclear-magnetic resonances of the medium in the first volume within the first measuring section. The measuring means is further designed to excite a second volume of the magnetized medium within the second measuring section to nuclear-magnetic resonances and to form a second signal sequence, in that the measuring means determines at least one signal characterizing the nuclear-magnetic resonances of the medium in the second volume within the second measuring section. Furthermore, the measuring means is designed, first, to determine a quotient sequence, in that the measuring means determines a quotient from each of the at least one signal of the first signal sequence and the at least one signal of the of the second signal sequence, and, second, to determine a velocity of the medium using the quotient sequence.

One design of the nuclear-magnetic flowmeter according to the invention provides that the measuring means is designed for carrying out one of the described methods.

The explanations in respect to the methods for operating nuclear-magnetic flowmeters are accordingly valid for the nuclear-magnetic flowmeters and vice versa.

In detail, there is a plurality of possibilities for designing and further developing the methods according to the invention and the nuclear-magnetic flowmeters according to the invention as will be apparent from the following description of preferred embodiments in conjunction with the accompanying drawings.

DETAILED DESCRIPTION OF THE INVENTION

Figure 1:
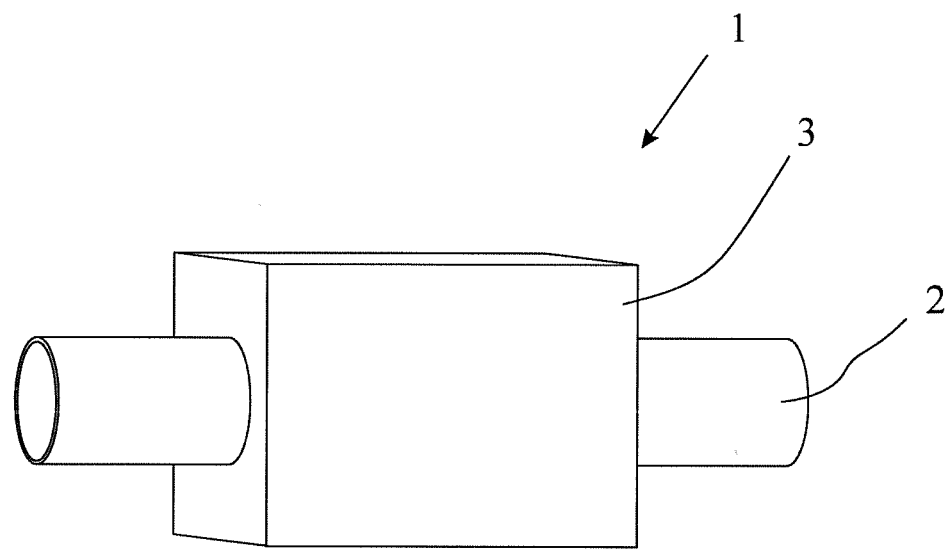
FIG. 1 is a perspective view of an embodiment of a nuclear magnetic flowmeter.

FIG. 1 shows, in an abstract, perspective representation, the nuclear-magnetic flowmeter 1. The nuclear-magnetic flowmeter 1 has the measuring tube 2 and a housing 3.

Figure 2:
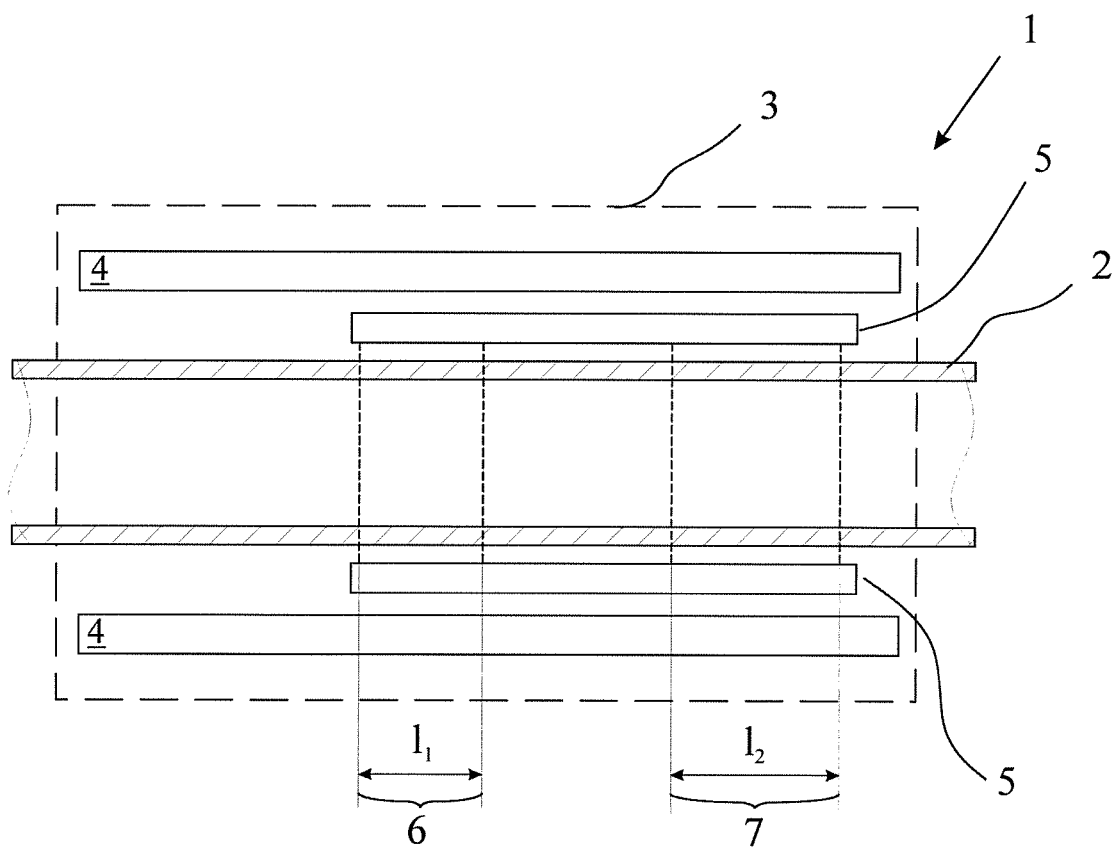
FIG. 2 is a longitudinal sectional view of the nuclear-magnetic flowmeter shown in FIG. 1.

FIG. 2 shows a longitudinal cut through the nuclear-magnetic flowmeter 1. The longitudinal cut allows for essential components of the nuclear-magnetic flowmeter 1 in the housing 3 to be seen. Thus, the nuclear-magnetic flowmeter 1 displays the magnetization means 4 and the measuring means 5 arranged in the housing 3. The measuring tube 2 thereby has the first measuring section 6 with the length $l_1$ and the second measuring section 7 with the length $l_2$, wherein the length $l_2$ of the second measuring section 7 is greater than the length $l_1$ of the first measuring section 6.

The magnetization means 4 is designed to permeate a medium flowing through the measuring tube 2 also over the first measuring section 6 and over the second measuring section 7 with a magnetic field. The magnetic field thereby magnetizes a medium so that it can be excited to nuclear-magnetic resonances.

The measuring means 5 is designed, first, during operation, to excite a medium magnetized by the magnetization means 4 to nuclear-magnetic resonances and, second, to determine signals that characterize the nuclear-magnetic resonances of the medium.

The measuring means 5, in this embodiment, first generates an electromagnetic pulse for exciting a magnetized medium in the measuring tube 2, the pulse being suitable for turning the vectors of the magnetic moment of the atomic nuclei of the magnetized medium to 90° in respect to a vector of the magnetic field. The nuclear-magnetic resonance excited by this electromagnetic pulse is a free induction decay and the measuring means 5 measures this free induction decay and, from this, determines a signal characterizing the free induction decay. The measurement of the signal is, in this embodiment, thereby carried out over an interval by the measuring means 5 and the measurement is integrated over the interval. As an alternative to integration, an average can be formed over the measurement.

After subsiding of the free induction decay, the magnetization means 4 excites the magnetized medium, then, to further nuclear-magnetic resonances. For this, in this embodiment, the measuring means 5 generates, in each case, an electromagnetic pulse that is suitable for turning the vectors of the magnetic moment of the atomic nuclei of the medium to 180° in respect to the vector of the magnetic field. In this manner, in each case, an echo signal is excited, which is measured by the measuring means 5. The measurements are thereby carried out as in the measurement of free induction decay.

The measuring means 5 is further designed to excite a magnetized medium within the first measuring section 6 and within the second measuring section 7 independent of one another to nuclear-magnetic resonances, to measure the nuclear-magnetic resonances and to determine signals from the measured nuclear-magnetic resonances characterizing them. Hereby, "independent of one another" means that either a magnetized medium within the first measuring section 6 and within the second measuring section 7 is excited and measured or that a magnetized medium within the first measuring section 6 or within the second measuring section 7 is excited and measured.

Figure 3:
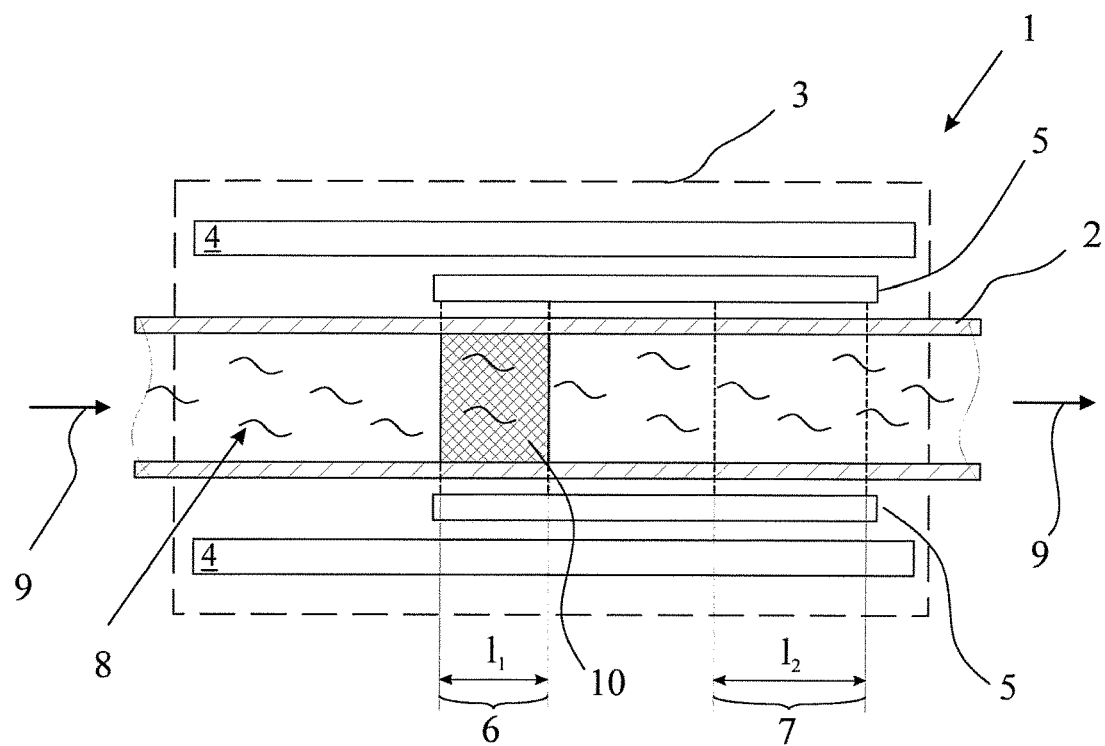
FIG. 3 is a longitudinal sectional view like that of FIG. 2 showing the nuclear-magnetic flowmeter during operation, implementing a first method at a first point in time.

FIGS. 3 to 6 show the nuclear-magnetic flowmeter 1 during operation at different points in time. FIG. 3 shows the nuclear-magnetic flowmeter 1 at a first point in time, FIG. 4 at a second point in time, FIG. 5 at a third point in time and FIG. 6 at a fourth point in time. The medium 8 thereby flows in direction 9 through the measuring tube 2, wherein it is magnetized by the magnetization means 4 so that it can be excited to nuclear-magnetic resonances. The measuring means 5 initially carries out a first method during operation of the nuclear-magnetic flowmeter 1. The first method requires only one measuring section and, in this embodiment, only the first measuring section 6 is used, however, the second measuring section 7 could just as easily be used instead of the first measuring section 6. A nuclear-magnetic flowmeter having only one, sole measuring section could also be used.

Figure 7:
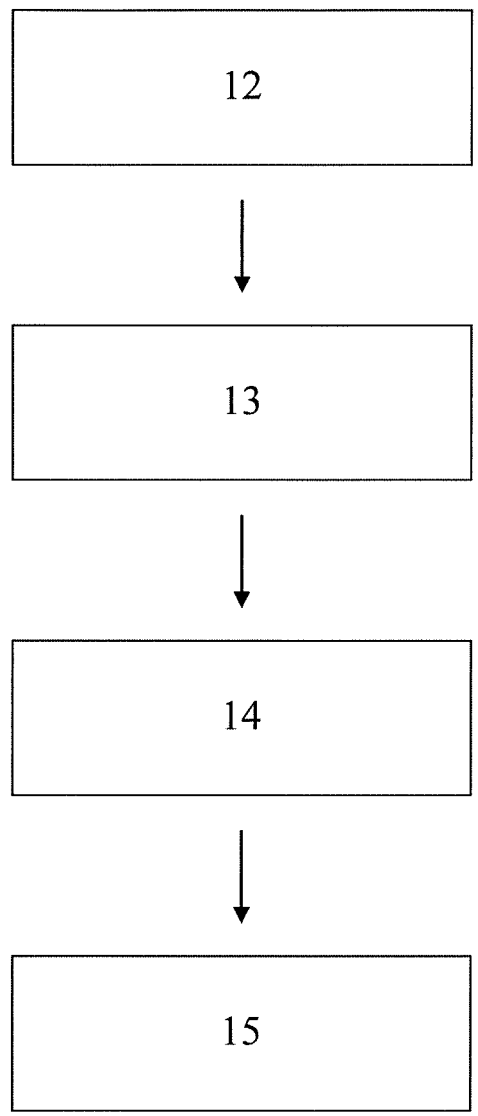
FIG. 7 is a flow chart of the first method.

The measuring means 5 carries out the first method, wherein the first method has the method steps shown in the flow chart in FIG. 7:

In the first method step 12, the first volume 10 of the magnetized medium 8 within the first measuring section 6 flowing at a first velocity is successively excited to three nuclear-magnetic resonances and a first signal sequence is formed. The first signal sequence is formed in that, for each of the nuclear-magnetic resonances of the medium 8, a signal characterizing the respective nuclear-magnetic resonance in the first volume 10 within the first measuring section 6 is determined. Thus, the first signal sequence has three signals.

At the first point in time shown in FIG. 3, the measuring means 5 excites the first volume 10 of the magnetized medium 8 over the entire length 1 of the first measuring section 6 to a free induction decay. The measurement for determining a first of the three signals is carried out on the excited medium 8 in volume 10, also over the entire length $l_1$ of the first measuring section 6.

Figure 4:
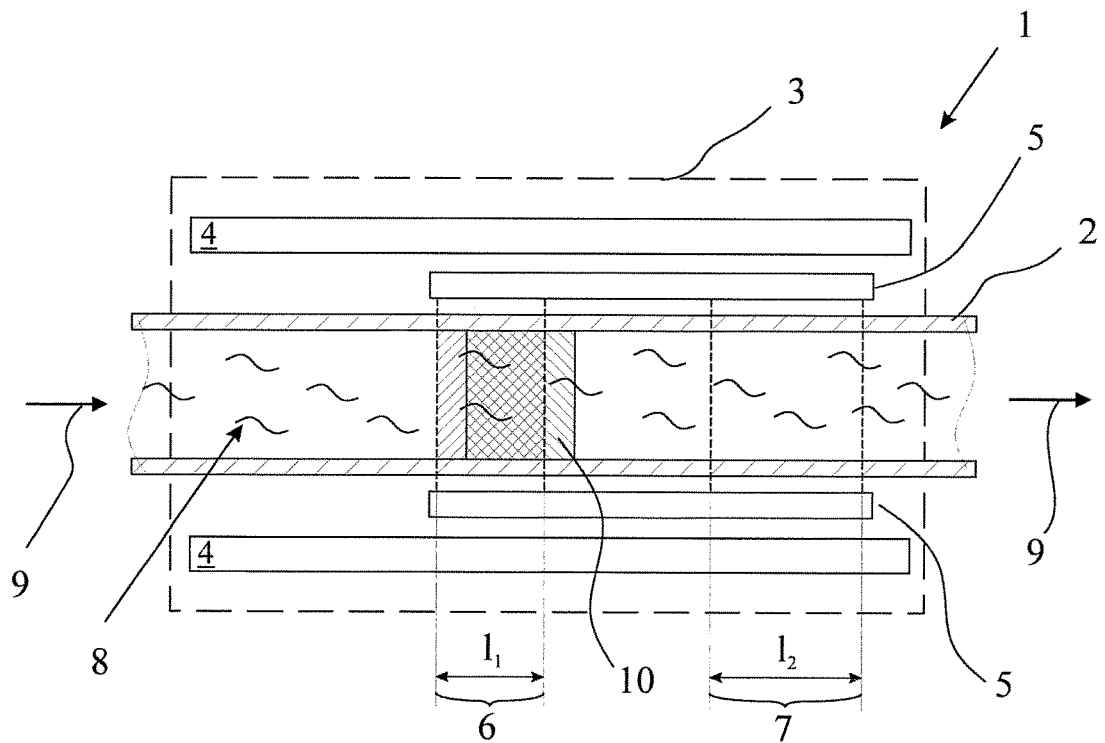
FIG. 4 is a longitudinal sectional view of the nuclear-magnetic flowmeter during operation, implementing the first method at a second point in time.

Between the first point in time shown in FIG. 3 and the second point in time shown in FIG. 4, a portion of the first volume 10 of the medium 8 flows out of the first measuring section 6 with the first velocity in direction 9. The portion of the first volume 10 of the medium 8 still remaining within the first measuring section 6 is indicated by a crosshatch pattern. At the second point in time, the measuring means 5 excites the portion of the first volume 10 of the magnetized medium 8 still remaining within the first measuring section 6 to a first echo signal. The measurement for determining a second of the three signals is carried out again over the entire length of the first measuring section 6. However, only the portion of the volume 10 of the medium 8 still remaining in the first measuring section 6 provides a contribution to the second signal.

Figure 5:
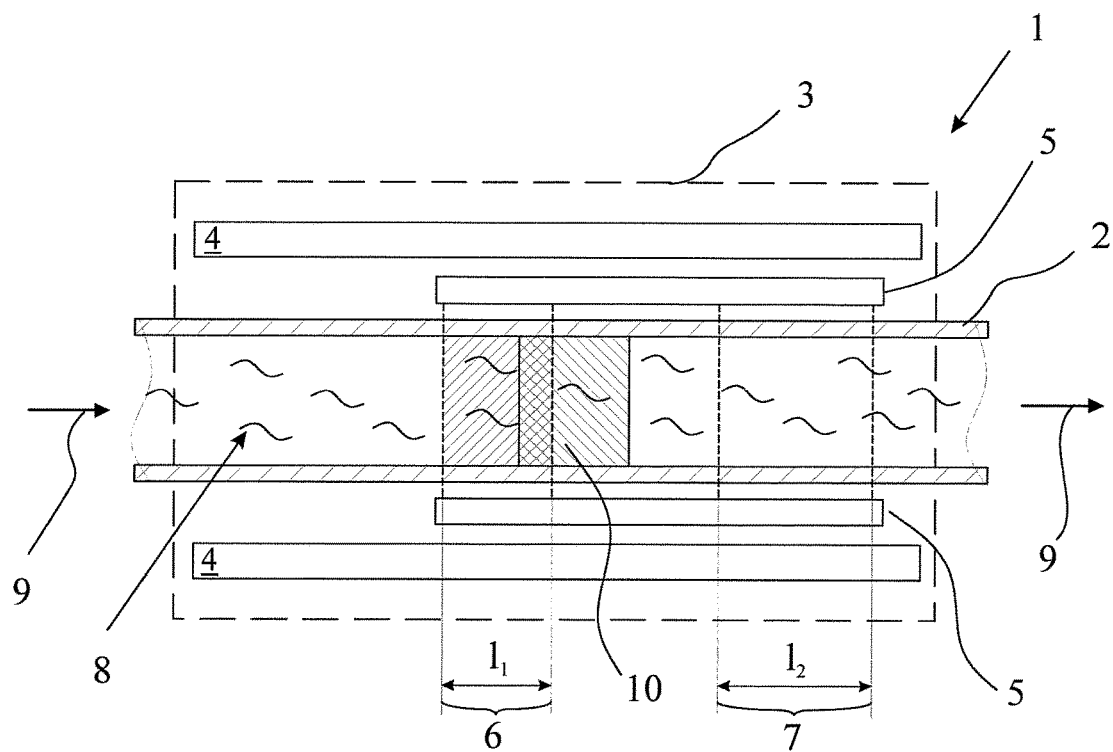
FIG. 5 is a longitudinal sectional view of the nuclear-magnetic flowmeter during operation, implementing the first method at a third point in time.

Between the second point of time shown in FIG. 4 and the third point in time shown in FIG. 5, a further portion of the first volume 10 of the medium 8 flows out of the first measuring section 6 with the first velocity in direction 9. The portion of the first volume 10 of the medium 8 still remaining within the first measuring section 6 at the third point in time is indicated, again, by a crosshatch pattern. At the third point in time, the measuring means 5 excites the portion of the first volume 10 of the medium 8 remaining in the first measuring section 6 to a second echo signal. The measurement for determining a third of the three signals is carried out, again, over the entire length $l_1$ of the first measuring section 6. However, again, only the portion of the volume 10 of the medium 8 remaining in the first measuring section 6 provides a contribution to the third signal.

The above explanations for the different points in time of the first method are accordingly universally valid for the described methods.

In the second method step 13, after carrying out the first method step 12, the second volume 11 of the magnetized medium 8 flowing at a second velocity within the first measuring section 6 is successively excited to three nuclear-magnetic resonances and a second signal sequence is formed. The second signal sequence is formed in that a signal characterizing the respective nuclear-magnetic resonance in the second volume 11 within the first measuring section 6 is determined for each of the nuclear-magnetic resonances of the medium 8. Thus, the second signal sequence also has three signals.

Figure 6:
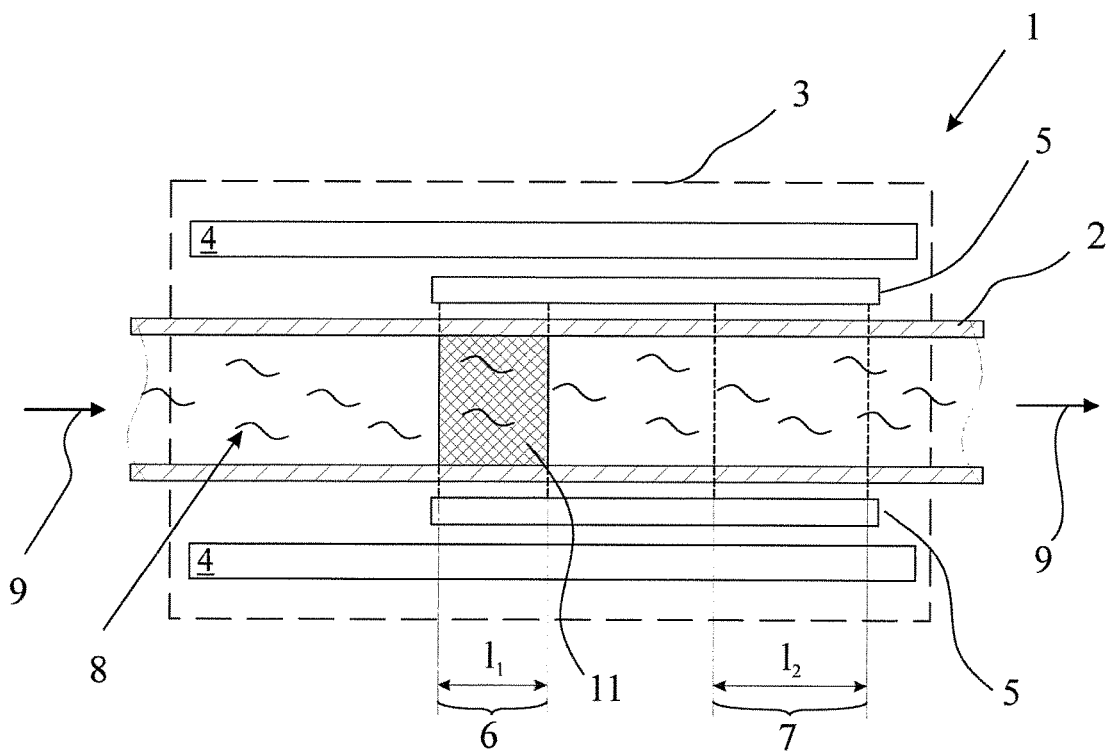
FIG. 6 is a longitudinal sectional view of the nuclear-magnetic flowmeter during operation, implementing the first method at a fourth point in time.

At the fourth point in time shown in FIG. 6, the measuring means 5 excites the second volume 11 of the magnetized medium 8 over the entire length of the first measuring section 6 to a free induction decay. The measurement for determining a first of the three signals is carried out on the excited medium 8 in volume 11 over the entire length $l_1$ of the first measuring section 6. The explanations for the first method step 12 apply to the rest.

In the third method step 14, a quotient sequence is determined, in that, in each case, a quotient is determined from the three signals of the first signal sequence and from the three signals of the second signal sequence. Thus, the quotient sequence has three quotients, wherein the first quotient is determined from the first signal of the first signal sequence and from the first signal of the second signal sequence, the second quotient is determined from the second signal of the first signal sequence and from the second signal of the second signal sequence and the third quotient is determined from the third signal of the first signal sequence and from the third signal of the second signal sequence.

In the fourth method step 15, the previously unknown first velocity and the previously unknown second velocity of the medium 8 are determined using the quotient sequence.

Figure 8:
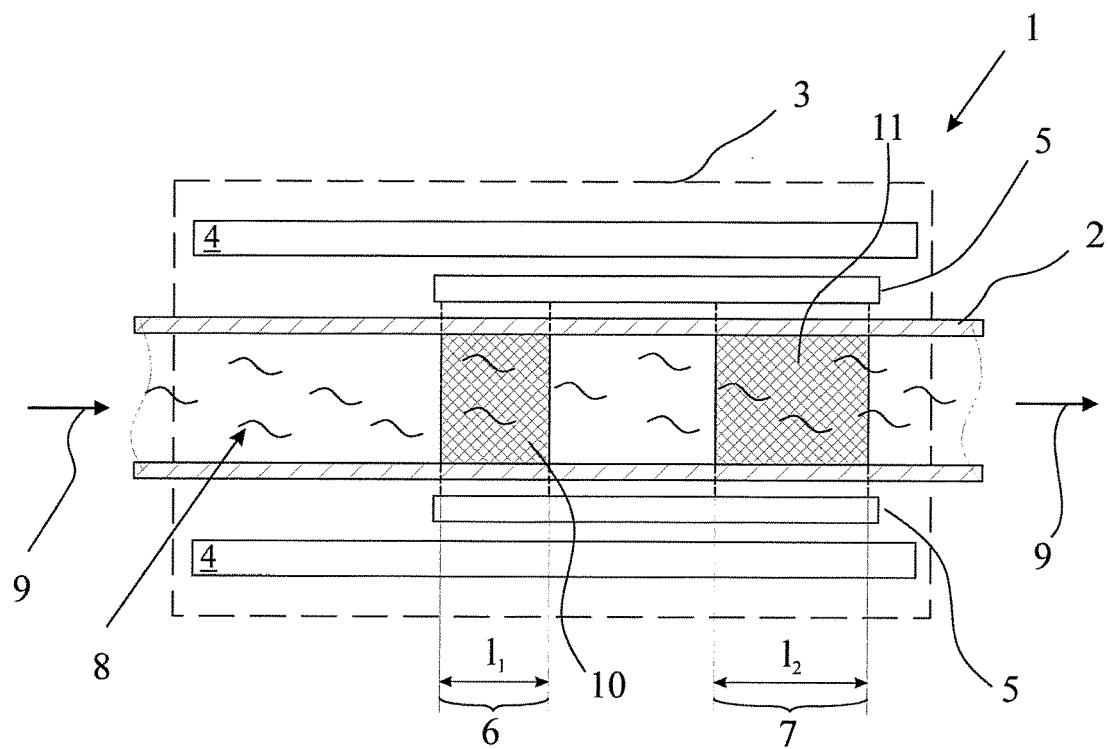
FIG. 8 is a longitudinal sectional view of the nuclear-magnetic flowmeter during operation, implementing a second method at a fifth point in time.
Figure 9:
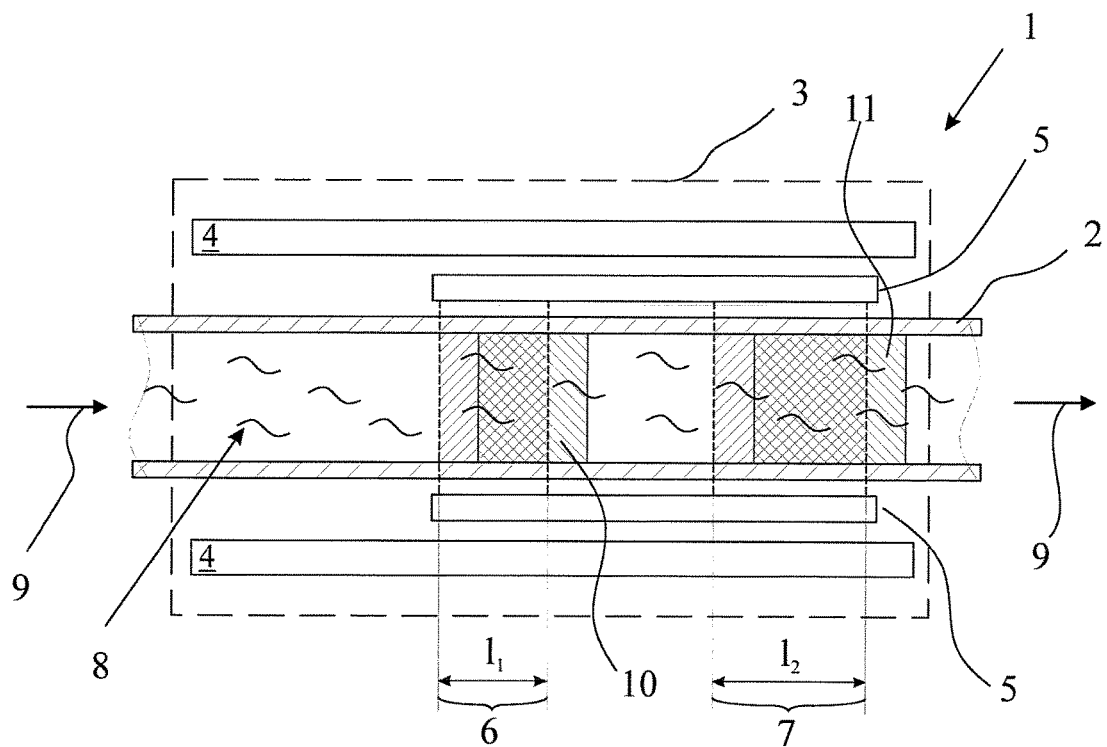
FIG. 9 is the longitudinal cut of the nuclear-magnetic flowmeter during operation, implementing the second method at a sixth point in time.

FIGS. 8 and 9 show the nuclear-magnetic flowmeter 1 during operating at further points in time. FIG. 8 shows the nuclear-magnetic flowmeter 1 at a fifth point in time and FIG. 9 at a later sixth point in time. The medium 8 thereby still flows in direction 9 through the measuring tube 2, wherein it is magnetized by the magnetization means 4 so that it can be excited to nuclear-magnetic resonances. The measuring means 5 now carries out a second method during operation of the nuclear-magnetic flowmeter 1. However, in contrast to the first method, the second method requires the second measuring section 7 in addition to the first measuring section 6.

Figure 10:
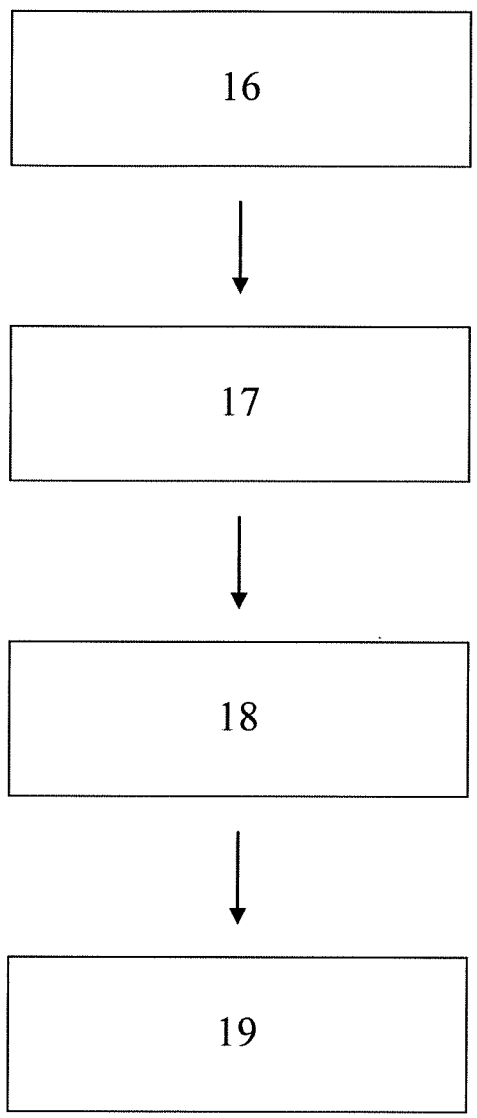
FIG. 10 is a flow chart of the second method.

The measuring means 5 carries out the second method, wherein the second method has the method steps shown in the flow chart in FIG. 10.

In the first method step 16, the first volume 10 of the magnetized medium 8 flowing at a velocity in the first measuring section 6 is successively excited to two nuclear-magnetic resonances and a first signal sequence is formed. The first signal sequence is formed in that a signal characterizing the respective nuclear-magnetic resonance in the first volume 10 within the first measuring section 6 is determined for each of the nuclear-magnetic resonances of the medium 8. Thus, the first signal sequence has two signals.

At a fifth point in time shown in FIG. 8, the measuring means 5 excites the first volume 10 of the magnetized medium 8 over the entire length of the first measuring section 6 to a free induction decay. The measurement for determining a first of the two signals is carried out on the excited medium 8 in the volume 10, also over the entire length $l_1$ of the first measuring section 6.

Between the fifth point in time shown in FIG. 8 and the sixth point in time shown in FIG. 9, a portion of the first volume 10 of the medium 8 flows out of the first measuring section 6 at a velocity in direction 9. The portion of the first volume 10 of the medium 8 still remaining within the first measuring section 6 is indicated by a crosshatch pattern. At the sixth point in time, the measuring means 5 excites the portion of the first volume 10 of the magnetized medium 8 still remaining within the first measuring section 6 to an echo signal. The measurement for determining a second of the two signals is carried out over the entire length $l_1$ of the first measuring section 6. However, only the portion of the volume 10 of the medium 8 still remaining in the first measuring section 6 provides a contribution to the second signal.

In the second method step 17, synchronous to the execution of the first method step 16, the second volume 11 of the magnetized medium 8 flowing at the velocity within the second measuring section 7 is successively excited to two nuclear-magnetic resonances and a second signal sequence is formed. The second signal sequence is formed in that a signal characterizing the respective nuclear-magnetic resonance in the second volume 11 within the second measuring section 7 is determined for each of the nuclear-magnetic resonances of the medium 8. Thus, the second signal sequence has two signals.

At a fifth point in time shown in FIG. 8, the measuring means 5 excites the second volume 11 of the magnetized medium 8 over the entire length $l_2$ of the second measuring section 7 to a free induction decay. The measurement for determining a first of the two signals is carried out on the excited medium 8 in the volume 11, also over the entire length $l_2$ of the second measuring section 7.

Between the fifth point in time shown in FIG. 8 and the sixth point in time shown in FIG. 9, a portion of the second volume 11 of the medium 8 flows out of the second measuring section 7 at the velocity in direction 9. The portion of the second volume 11 of the medium 8 still remaining within the second measuring section 7 is indicated by a crosshatch pattern. At the sixth point in time, the measuring means 5 excites the portion of the second volume 11 of the magnetized medium 8 still remaining within the second measuring section 7 to an echo signal. The measurement for determining a second of the two signals is carried out over the entire length $l_2$ of the second measuring section 7. However, only the portion of the volume 11 of the medium 8 still remaining in the second measuring section 7 provides a contribution to the second signal.

The above explanations for the different points in time of the second method are accordingly universally valid for the described methods.

In the third method step 18, a quotient sequence is determined in that, in each case, a quotient is determined from the two signals of the first signal sequence and from the two signals of the second signal sequence. Thus, the quotient sequence has two quotients, wherein the first quotient is determined from the first signal of the first signal sequence and the first signal of the second signal sequence and the second quotient is determined from the second signal of the first signal sequence and the second signal of the second signal sequence.

In the fourth method step 19, the previously unknown velocity of the medium 8 is determined using the quotient sequence.

The explanations in respect to the first method hold true for the rest.

What is claimed is:

1. Method for operating a nuclear-magnetic flowmeter, wherein the nuclear-magnetic flowmeter has a measuring tube with a first measuring section through which a medium is made to flow and in which the medium is magnetized, the method comprising:

exciting a first volume of magnetized medium flowing at a first velocity within the first measuring section to nuclear-magnetic resonances and forming a first signal sequence having at least one signal relating to the nuclear-magnetic resonances of the medium in the first volume within the first measuring section, exciting a second volume of the magnetized medium flowing at a second velocity within the first measuring section to nuclear-magnetic resonances and forming a second signal sequence having at least one signal relating to the nuclear-magnetic resonances of the medium in the second volume within the first measuring section are determined, determining a quotient sequence from at least one signal of the first signal sequence and at least one signal of the second signal sequence, and determining at least one of the first velocity and the second velocity using the quotient sequence.

2. Method according to claim 1, wherein a free induction decay is measured as the at least one signal of at least one of the first signal sequence and the second signal sequence.

3. Method according to claim 2, wherein an echo signal is measured as at least one further signal of at least one of the first signal sequence and the second signal sequence.

4. Method for operating a nuclear-magnetic flowmeter, wherein the nuclear-magnetic flowmeter has a measuring tube with a first measuring section and a second measuring section through which a medium is made to flow and in which the medium is magnetized, the method comprising:

exciting a first volume of the magnetized medium within the first measuring section to nuclear-magnetic resonances and forming a first signal sequence with at least one signal characterizing the nuclear-magnetic resonances of the medium in the first volume within the first measuring section, exciting a second volume of the magnetized medium within the second measuring section to nuclear-magnetic resonances and forming a second signal sequence having at least one signal characterizing the nuclear-magnetic resonances of the medium in the second volume within the second measuring section is determined, determining a quotient sequence from each signal of the first signal sequence and each signal of the of the second signal sequence, and that a velocity of the medium is determined using the quotient sequence.

5. Method according to claim 4, wherein a free induction decay is measured as the at least one signal of at least one of the first signal sequence and the second signal sequence.

6. Method according to claim 5, wherein an echo signal is measured as at least one further signal of at least one of the first signal sequence and the second signal sequence.

7. Method according to claim 4, wherein, for determining the at least one signal in at least one of the first signal sequence and the second signal sequence, a measurement is carried out on the medium over an interval and the measurement is integrated over the interval or an average is formed over the measurement.

8. Method according to claim 4, wherein at least one of the first signal sequence and the second signal sequence have at least two signals that are determined.

9. Method according to claim 6, wherein the quotient sequence is interpolated by a function.

10. Method according to claim 9, wherein the function is determined from a product of several base functions.

11. Method according to claim 10, wherein polynomial functions and exponential functions are used as the base functions.

12. Method according to claim 8, wherein the quotient sequence is approximated using a Taylor polynomial.

13. Method according to claim 12, wherein a temperature of the medium is determined and the temperature is used in determination of the quotient sequence.

14. Method according to claim 13, wherein a spin-spin relaxation time constant of the medium is determined using at least one the quotient sequence, the at least one signal of the first signal sequence or the at least one signal of the second signal sequence.

15. Nuclear-magnetic flowmeter, comprising:

a measuring tube through which a medium flows during operation and having a first measuring section, a magnetization means which magnetizes the medium in the measuring tube during operation, and a measuring means for, during operation:

exciting a first volume flowing at a first velocity of the magnetized medium within the first measuring section to nuclear-magnetic resonances, forming a first signal sequence, and determining at least one signal characterizing the nuclear-magnetic resonances of the medium in the first volume within the first measuring section, then, exciting a second volume flowing at a second velocity of the magnetized medium within the first measuring section to nuclear-magnetic resonances, forming a second signal sequence, and determining at least one signal characterizing the nuclear-magnetic resonances of the medium in the second volume within the first measuring section, and determining a quotient sequence in which a quotient is determined from each signal of the first signal sequence and of the second signal sequence, and determining at least one of the first velocity and second velocity using the quotient sequence.

16. Nuclear-magnetic flowmeter, comprising:

a measuring tube through which a medium flows during operation and having a first measuring section and a second measuring section, a magnetization means which magnetizes the medium in the measuring tube during operation, and a measuring means for, during operation:

exciting a first volume of the magnetized medium within the first measuring section to nuclear-magnetic resonances, forming a first signal sequence, and determining at least one signal characterizing the nuclear-magnetic resonances of the medium in the first volume within the first measuring section, exciting a second volume of the magnetized medium within the second measuring section to nuclear-magnetic resonances, forming a second signal sequence, determining at least one signal characterizing the nuclear-magnetic resonances of the medium in the second volume within the second measuring section, determining a quotient sequence from each signal of the first signal sequence and the second signal sequence, and determining a velocity of the medium using the quotient sequence.

* * * * *